(12) United States Patent
Harada et al.

(10) Patent No.: US 12,202,786 B2
(45) Date of Patent: Jan. 21, 2025

(54) METHOD FOR PRODUCING AROMATIC NITRILE COMPOUND AND METHOD FOR PRODUCING CARBONATE ESTER

(71) Applicant: MITSUBISHI GAS CHEMICAL COMPANY, INC., Tokyo (JP)

(72) Inventors: Hidefumi Harada, Tokyo (JP); Takehiko Isobe, Tokyo (JP); Keisuke Shimokawa, Tokyo (JP); Ryotaro Umezu, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 18/140,333

(22) Filed: Apr. 27, 2023

(65) Prior Publication Data

US 2023/0348367 A1 Nov. 2, 2023

Related U.S. Application Data

(62) Division of application No. 17/261,612, filed as application No. PCT/JP2019/029164 on Jul. 25, 2019, now Pat. No. 11,673,856.

(30) Foreign Application Priority Data

Jul. 27, 2018 (JP) ................................. 2018-141487

(51) Int. Cl.
| | | |
|---|---|---|
| *C07C 253/20* | (2006.01) | |
| *B01J 23/04* | (2006.01) | |
| *B01J 23/10* | (2006.01) | |
| *C07C 68/04* | (2006.01) | |
| *C07D 213/84* | (2006.01) | |

(52) U.S. Cl.
CPC ............. *C07C 253/20* (2013.01); *B01J 23/04* (2013.01); *B01J 23/10* (2013.01); *C07C 68/04* (2013.01); *C07D 213/84* (2013.01)

(58) Field of Classification Search
USPC ........................................................ 546/286
See application file for complete search history.

(56) References Cited

U.S. PATENT DOCUMENTS

| 4,026,901 | A | 5/1977 | Coffen |
| 5,214,162 | A | 5/1993 | Nösberger |
| 6,248,917 | B1 | 6/2001 | Kleemiss |
| 10,793,524 | B2 | 10/2020 | Harada et al. |
| 2020/0282389 | A1 | 3/2020 | Harada et al. |
| 2020/0392085 | A1 | 12/2020 | Harada et al. |
| 2021/0061749 | A1 | 3/2021 | Harada et al. |

FOREIGN PATENT DOCUMENTS

| DE | 1 279 020 B | 10/1968 |
| JP | 04-321672 A | 11/1992 |
| JP | 09-003030 A | 1/1997 |
| JP | 2010-077113 A | 4/2010 |
| JP | 2012-162523 A | 8/2012 |
| JP | 2016-216361 A | 12/2016 |
| WO | 1991/001298 | 2/1991 |
| WO | 2015/099053 A1 | 7/2015 |
| WO | 2018/116775 A1 | 6/2018 |
| WO | 2019065549 A1 | 4/2019 |
| WO | 2019/138993 A1 | 7/2019 |

OTHER PUBLICATIONS

International Search Report issued in International Patent Application No. PCT/JP2019/029164, dated Oct. 15, 2019, along with an English translation thereof.
Written Opinion of the International Searching Authority issued in International Patent Application No. PCT/JP2019/029164, dated Oct. 15, 2019, along with an English translation thereof.
Extended European Search Report issued in corresponding European Patent Application No. 19840326.3 dated Mar. 24, 2021.
J. Campbell et al., "Laboratory-Scale Synthesis of Nitriles by Catalysed Dehydration of Amides and Oximes under Flash Vacuum Pyrolysis (FVP) Conditions", Synthesis 2007, No. 20, p. 3179-3184, XP055494863.
Office Action issued in corresponding Singapore Patent Application No. 11202012997Y dated Mar. 18, 2022.

*Primary Examiner* — Taofiq A Solola
(74) *Attorney, Agent, or Firm* — GREENBLUM & BERNSTEIN, P.L.C.

(57) ABSTRACT

The present invention provides a method for producing an aromatic nitrile compound, the method comprising a dehydration reaction wherein a desired compound can be selectively obtained with high yield while suppressing the generation of by-products during the regeneration of an aromatic amide compound into the corresponding aromatic nitrile compound. In addition, the present invention realizes a method for efficiently producing a carbonate ester by applying the abovementioned production method to a method for producing a carbonate ester. The above are achieved by means of a method for producing an aromatic nitrile compound involving a dehydration reaction wherein an aromatic amide compound is dehydrated, the method having a contact step for bringing the aromatic amide compound into contact with a catalyst in a gas phase during the dehydration reaction.

5 Claims, 2 Drawing Sheets

METHOD FOR PRODUCING AROMATIC NITRILE COMPOUND AND METHOD FOR PRODUCING CARBONATE ESTER

CROSS REFERENCE TO RELATED APPLICATION

This is a divisional application of U.S. patent application Ser. No. 17/261,612, filed on Jan. 20, 2021, which is a U.S. National Stage entry of PCT/JP2019/029164, filed on Jul. 25, 2019, and which claims the benefit of Japanese Patent Application No. 2018-141487, filed on Jul. 27, 2018. The disclosure of each of the above-identified applications, including the specification, drawings, and claims, is incorporated herein by reference in its entirety.

TECHNICAL FIELD

The present invention relates to a method for producing an aromatic nitrile compound such as cyanopyridine and a method for producing a carbonate ester.

BACKGROUND ART

"Carbonate ester" is a general term for a compound obtained by substituting one or both of two hydrogen atoms in carbonic acid $CO(OH)_2$ with an alkyl group or an aryl group, and it has a structure of RO—C(═O)—OR' (R and R' represent a saturated hydrocarbon group or an unsaturated hydrocarbon group).

A carbonate ester is used as an additive, for example, a gasoline additive for improving the octane value and a diesel fuel additive for decreasing the amount of particles in exhaust gas. A carbonate ester is also used as, for example, an alkylation agent, a carbonylation agent, a solvent or the like for synthesizing resins or organic compounds such as polycarbonate, urethane, pharmaceutical drugs, agricultural chemicals or the like, a material of an electrolytic solution of lithium ion cells, a material of lubricant oil, or a material of an oxygen absorber for rust inhibition of boiler pipes. As can be seen, a carbonate ester is a very useful compound.

As a conventional method for producing a carbonate ester, a method for directly reacting phosgene, which is used as a source of a carbonyl, with an alcohol is mainly employed. Phosgene used in this method is highly hazardous and highly corrosive, and therefore, needs extreme caution when being handled, for example, transported or stored. It is highly costly to control and manage, and guarantee the safety of, production facilities of phosgene. Further, in the case of the production using this method, raw materials and catalysts contain halogen such as chlorine, and the obtained carbonate ester contains a trace amount of halogen, which cannot be removed by a simple purification step. When the carbonate ester is used for a gasoline additive, a light oil additive or an electronic material, such halogen may undesirably cause corrosion. For this reason, a thorough purification step is indispensable to decrease the trace amount of halogen present in the carbonate ester to the level of an extremely trace amount. Moreover, recently, administrative offices provide a strict administration guidance and do not permit new establishment of production facilities using this method because this method utilizes phosgene, which is highly hazardous to the human body. Accordingly, a new method for producing a carbonate ester that does not use phosgene is strongly desired.

A method for directly synthesizing a carbonate ester from an alcohol and carbon dioxide using a heterogeneous catalyst is also known. Regarding this method, studies had been made on using 2-cyanopyridine or benzonitrile as a wettable powder to significantly improve the production amount and the production speed of the carbonate ester, to allow the reaction to advance easily under a pressure close to ordinary pressure, and to increase the reaction speed (see Patent Documents 1 and 2). However, there was a problem regarding the method for treating or utilizing benzamide or the like generated as a by-product.

For example, use of benzamide generated by the reaction between benzonitrile and water is limited to some of pharmaceutical and agrochemical intermediates. Thus, use of benzamide is limited to some extent. Therefore, in the production of a carbonate ester using benzonitrile as a wettable powder, benzamide by-produced is desired to be regenerated into benzonitrile and reused. It is now an issue to realize a regeneration reaction with high selectivity (because it is considered that if a by-product is generated, it is difficult to reuse benzonitrile as a wettable powder) and a high yield (because if the yield is low, benzamide remains in a large amount, which increases the amount of work, namely, work load, of separating benzamide and benzonitrile from each other).

In consideration of the above-described problems regarding the regeneration of benzamide or the like into benzonitrile or the like, there is a known method for performing the above-described regeneration not using a strong reagent while suppressing the generation of a by-product (Patent Document 3).

However, according to this method, generation of nitrile by means of dehydration of an amide compound requires 400 hours and therefore cannot be balanced with, namely, cannot be used in combination with, a carbonate ester synthesis reaction, which requires only 24 hours. This method also has a problem that steps of extraction, infiltration and the like are necessary for solid-liquid separation of a catalyst, resulting in a complicated process having many steps.

PRIOR ART DOCUMENTS

Patent Documents

Patent Document 1: Japanese Laid-Open Patent Publication No. 2010-77113
Patent Document 2: Japanese Laid-Open Patent Publication No. 2012-162523
Patent Document 3: WO2015/099053

SUMMARY OF THE INVENTION

Problems to be Solved by the Invention

In consideration of the above-described problems of prior art, an object of the present invention is to provide a method which enables a dehydration reaction, wherein a desired compound can be selectively obtained with high yield while suppressing the generation of by-products during the regeneration of an aromatic amide compound such as pyridinecarboamide into cyanopyridine that is a corresponding aromatic nitrile compound. Another object of the present invention is to provide a method for producing an aromatic nitrile compound, which can decrease the number of steps of the dehydration reaction and significantly improve the reaction speed to shorten the reaction time.

A still another object of the present invention is to apply the above-described method for producing an aromatic nitrile compound to a carbonate ester production method to realize a method for efficiently producing a carbonate ester.

Means for Solving the Problems

In order to solve the above-described problems, the present inventors made researches regarding a method for producing an aromatic nitrile compound such as cyanopyridine by means of dehydration of an aromatic amide compound. The present inventors examined reaction conditions for dehydration of the aromatic amide compound, and realized a dehydration reaction process, wherein, by bringing the aromatic amide compound in the form of gas or mist into contact with a catalyst in a gas phase in a short time, the reaction speed can be significantly improved to shorten the reaction time, and in addition, a desired compound can be selectively obtained with high yield while suppressing the generation of by-products.

According to the above-described present invention, it is possible to improve the rate of regeneration of the aromatic amide compound into the aromatic nitrile compound by means of the dehydration reaction, and the dehydration reaction and the rate of synthesis of a carbonate ester from $CO_2$ and an alcohol using the aromatic nitrile compound can be established as a series of efficient commercial processes. The present inventors also made researches for applying the above-described finding to a carbonate ester production method. As a result, also in a method for producing a carbonate ester in which the carbonate ester is directly synthesized from an alcohol and carbon dioxide, it was confirmed that beneficial effects are obtained when an aromatic nitrile compound is efficiently regenerated by a contact step in which an aromatic amide compound in the form of gas or mist is brought into contact with a catalyst in a gas phase in a short time. The gist of the present invention is as described below.

(1) A method for producing an aromatic nitrile compound, the method comprising a dehydration reaction, wherein an aromatic amide compound is dehydrated, the method having a contact step for bringing the aromatic amide compound into contact with a catalyst in a gas phase during the dehydration reaction.

(2) The method for producing an aromatic nitrile compound according to item (1), wherein the catalyst includes an alkali metal.

(3) The method for producing an aromatic nitrile compound according to item (1) or (2), wherein the aromatic amide compound includes at least a heteroaryl amide compound, and wherein the aromatic nitrile compound includes at least a heteroaryl nitrile compound.

(4) The method for producing an aromatic nitrile compound according to item (3), wherein the heteroaryl amide compound includes 2-picolinamide, and wherein the heteroaryl nitrile compound includes 2-cyanopyridine.

(5) The method for producing an aromatic nitrile compound according to any one of items (1) to (4), wherein in the contact step, an inert gas and/or a solvent in a vaporized state is further brought into contact with the catalyst.

(6) The method for producing an aromatic nitrile compound according to item (5), wherein the inert gas includes at least nitrogen gas.

(7) The method for producing an aromatic nitrile compound according to item (5) or (6), wherein the boiling point of the solvent under ordinary pressure is 20° C. to 300° C.

(8) The method for producing an aromatic nitrile compound according to any one of items (5) to (7), wherein the solvent is compatible with the aromatic amide compound.

(9) The method for producing an aromatic nitrile compound according to any one of items (5) to (8), wherein the solvent includes a pyridine compound and/or a cyclic ketone.

(10) The method for producing an aromatic nitrile compound according to any one of items (1) to (9), wherein in the contact step, the temperature at which the aromatic amide compound is brought into contact with the catalyst in the gas phase is 170° C. or higher but lower than 300° C.

(11) The method for producing an aromatic nitrile compound according to any one of items (1) to (10), wherein the time for bringing the aromatic amide compound into contact with the catalyst in the gas phase is 0.001 sec or more but less than 10 sec.

(12) A method for producing a carbonate ester, which has:
a first reaction step that includes: a carbonate ester production reaction in which an alcohol is reacted with carbon dioxide in the presence of an aromatic nitrile compound to produce the carbonate ester and water, and a hydration reaction in which the aromatic nitrile compound is hydrated with the produced water to produce an aromatic amide compound; and
a second reaction step in which the aromatic amide compound is separated from the reaction system of the first reaction step and then the aromatic amide compound is regenerated into an aromatic nitrile compound by means of a dehydration reaction for dehydrating the aromatic amide compound, the dehydration reaction having a contact step for bringing the aromatic amide compound into contact with a catalyst in a gas phase,
wherein at least a part of the aromatic nitrile compound regenerated in the second reaction step is used in the first reaction step.

(13) The method for producing a carbonate ester according to item (12), wherein in the second reaction step, an aromatic nitrile compound is produced from the aromatic amide compound according to the method for producing an aromatic nitrile compound according to any one of items (2) to (11) to regenerate the aromatic nitrile compound.

(14) The method for producing a carbonate ester according to item (12) or (13), wherein a catalyst including cerium oxide is used in the carbonate ester production reaction.

(15) The method for producing a carbonate ester according to any one of items (12) to (14), wherein the alcohol includes an alcohol having 1 to 6 carbon atoms.

Advantageous Effect of the Invention

According to the present invention, it is possible to efficiently carry out the production (regeneration) of an aromatic nitrile compound such as cyanopyridine from an aromatic amide compound such as pyridinecarboamide (picolinamide, nicotinamide, etc.) and benzamide. Specifically, in a dehydration reaction of the aromatic amide compound for the above-described regeneration, the generation of by-products can be suppressed, a desired compound can be selectively obtained with high yield, and a reaction rate can be improved. Therefore, according to the present invention, the reaction time of the dehydration reaction for regenerating the aromatic nitrile compound can be significantly reduced when compared to conventional methods. Moreover, by employing a gas phase reaction, the size of a reaction container can be reduced more when compared to the step of dehydration of an amide compound using a conventional liquid phase reaction. Therefore, according to the present invention, the step of regenerating the corresponding aromatic nitrile compound from the aromatic amide compound can be easily industrialized.

Furthermore, according to the present invention, by producing the aromatic nitrile compound as described above, a method for efficiently producing a carbonate ester can also be realized.

EMBODIMENTS FOR CARRYING OUT THE INVENTION

Hereinafter, preferred embodiments of the present invention will be described in detail.

<1. Method for Producing Aromatic Nitrile Compound>

In the method for producing an aromatic nitrile compound of the present invention, an aromatic amide compound such as pyridinecarboamide (2-pyridinecarboamide, 3-pyridinecarboamide or 4-pyridinecarboamide) is dehydrated in a gas phase and converted into an aromatic nitrile compound such as cyanopyridine. Specifically, in the method for producing an aromatic nitrile compound of the present invention, for example, a dehydration reaction is caused by a contact step in which the aromatic amide compound is brought into contact with a catalyst carrying a basic metal oxide in a gas phase, thereby producing the aromatic nitrile compound.

(Reaction Substrate)

Examples of the aromatic amide compound to be used in the method for producing an aromatic nitrile compound include amide compounds having an aromatic hydrocarbon ring such as a benzene ring, a naphthalene ring and an anthracene ring or a heteroaryl ring. Among these aromatic amide compounds, an aromatic amide compound having a heteroaryl ring, i.e., a heteroaryl amide compound is preferably used, and examples of the heteroaryl amide compound include amide compounds having a pyridine ring, a pyrimidine ring, a pyridazine ring, a pyrazine ring, a triazine ring, a pyrrole ring, a furan ring, a thiophene ring, an imidazole ring, a pyrazole ring, an oxazole ring or the like.

Preferred specific examples of the heteroaryl amide compound include those having a pyridine ring such as pyridinecarboamide (2-pyridinecarboamide, 3-pyridinecarboamide and 4-pyridinecarboamide) described above.

The aromatic nitrile compound produced by the production method of the present invention is a product of a dehydration reaction corresponding to the above-described aromatic amide compound as is clear from the above-described reaction formula. Accordingly, specific examples of the aromatic nitrile compound targeted in the production method of the present invention include a heteroaryl nitrile compound. Preferred specific examples of the heteroaryl nitrile compound include those having a pyridine ring such as cyanopyridine (2-cyanopyridine, 3-cyanopyridine and 4-cyanopyridine).

(Catalyst)

In this regard, the catalyst to be used in the above-described dehydration reaction of the present invention preferably includes an oxide of an alkali metal (K, Li, Na, Rb, Cs). In particular, as the catalyst to be used in the above-described reaction, a catalyst including an oxide of at least one of Na, K, Rb and Cs (cesium) is preferably used. Further, as a carrier of the above-described catalyst, a substance generally serving as a catalyst carrier can be used, but as a result of examination of various carriers, it is preferred that $SiO_2$ or $ZrO_2$ is included.

An example of the method for producing the catalyst to be used in the dehydration reaction of the present invention will be described below. In the case where the carrier is $SiO_2$, a commercially available powdered or spherical $SiO_2$ can be used, and it is preferred that the particle size is adjusted to, for example, 4.0 mm or less so that an active metal can be uniformly carried, and that pre-baking is carried out in the air at 700° C. for 1 hour for removing moisture. There are $SiO_2$ products with various characteristics, but the larger the specific surface area is, the better it is because the active metal can be highly dispersed and the amount of the aromatic nitrile compound produced is improved. Specifically, the specific surface area is preferably 300 $m^2$/g or more. However, the specific surface area of the catalyst after preparation may be reduced to be less than the specific surface area of $SiO_2$ alone due to the interaction between $SiO_2$ and the active metal or the like. In this case, the specific surface area of the catalyst after the production is preferably 150 $m^2$/g or more. A metal oxide serving as an active species can be carried according to an impregnation method such as an incipient wetness method and an evaporation drying method.

It is sufficient when a metal salt that is a precursor of the catalyst is water-soluble, and when it is an alkali metal, various compounds such as a carbonate, a hydrogencarbonate, a chloride salt, a nitrate and a silicate can be used. A carrier is impregnated with an aqueous solution of a precursor of a basic metal, followed by drying and baking, and then the obtained product can be used as the catalyst. The baking temperature varies depending on the precursor to be used, but it is preferably 400 to 600° C.

Further, as the catalyst to be used in the present invention, a catalyst in which only one or more alkali metal oxides are carried on a carrier consisting of one or both of $SiO_2$ and $ZrO_2$ is preferred, but other than the above-described elements, the catalyst may contain an unavoidable impurity mixed during the catalyst production process or the like. However, it is desirable that mixing of an impurity is suppressed as much as possible.

In this regard, the catalyst to be used in the present invention, wherein a metal oxide serving as an active species is carried on a carrier, may be in the form of either powder or a molded body, and in the case of the molded body, it may be any of a spherical type, a pellet type, a cylinder type, a ring type, a wheel type, a granular type, etc. Further, the catalyst can be fixed to a support structure such as a honeycomb and used.

The size of the carrier is not limited, but when using a spherical carrier, the average diameter of particles of the catalyst (carrier diameter) is preferably 0.01 to 8.0 mm, more preferably 0.03 to 6.0 mm, and even more preferably 0.05 to 5.0 mm. By using the catalyst whose carrier diameter is relatively larger than the average diameter (carrier diameter) of particles of a catalyst to be used in a liquid phase reaction as described above, the flow channel of the reaction substrate in the gas phase reaction is ensured, and a high space velocity can be provided. Note that when using a fluidized bed in the gas phase reaction, a catalyst with a relatively small particle diameter is preferably used so that the catalyst can be stirred with a small gas flow amount, and that when using a fixed bed in the gas phase reaction, a relatively large particle diameter or shape is preferred so that the generation of pressure loss can be prevented as much as possible.

The carrier diameter, i.e., the average diameter of particles of the catalyst refers to the average diameter of particles of the whole catalyst including a catalytic component and the carrier. The value of the carrier diameter of the catalyst is measured based on the sieving method: Test sieving—General requirements defined in JISZ8815 or the like.

Further, the carrying amount of the catalyst may be suitably set, but based on the total catalyst weight, the carrying amount in metal conversion of the active species such as an alkali metal oxide is preferably 0.05 to 2.0 mmol/g, more preferably 0.10 to 1.5 mmol/g, and even more preferably 0.30 to 1.0 mmol/g. Further, the amount of the catalyst used during the reaction may also be suitably set.

(Reaction System and Reaction Container)

In the method for producing the aromatic nitrile compound of the present invention, it is preferred to use a gas phase reaction in which an amide compound in the form of gas or mist is flowed through a catalyst layer together with an inert gas, and a gas phase reaction apparatus with a fixed bed or fluidized bed can be applied thereto. Thus, in the contact step in which the aromatic amide compound is brought into contact with the catalyst in the gas phase, the aromatic amide compound in a completely vaporized state is preferably used, but the aromatic amide compound in a state where mist is partially included in gas may also be used.

It is desirable that the method for producing the aromatic nitrile compound is performed while removing produced by-product water by means of a dehydration reaction. The present inventors diligently made researches and found that, for example, when a vaporizing chamber is attached to the upper portion of a reaction tube in which the catalyst is put, the aromatic amide compound is dropped into the vaporizing chamber and the amide compound is passed through the catalyst layer in the gas phase in a short time, the amount of the aromatic nitrile compound produced can be improved, and the production of a by-product can be suppressed.

(Inert Gas)

In the above-described dehydration reaction, it is preferred that an inert gas is brought into contact with the catalyst together with the aromatic amide compound in the gas phase. Specific examples of the inert gas to be used in the dehydration reaction include nitrogen gas and rare gases such as helium and argon, and nitrogen gas is preferably used. The flow rate, etc. of the inert gas will be described later.

(Solvent)

In the above-described dehydration reaction, a solvent can be used. In particular, in the step of vaporizing the aromatic amide compound whose melting point is high, by mixing the aromatic amide compound with a solvent compatible therewith in advance and delivering the mixture, the trouble of closure due to precipitation of the aromatic amide compound can be prevented. That is, it is preferred to use a solvent that is compatible with the aromatic amide compound as the target of the dehydration reaction. The solvent compatible with the aromatic amide compound includes not only a solvent which can be mixed with the aromatic amide compound at any ratio, but also a solvent which can dissolve the aromatic amide compound as the target only to a predetermined degree of solubility, in an amount by which the aromatic amide compound can be dissolved to a concentration that is equal to or lower than the upper limit of the degree of solubility at a predetermined temperature. Further, it is preferred that the solvent is also vaporized and used in the dehydration reaction (contact step). The boiling point of the solvent that is vaporized and used in the dehydration reaction as described above is preferably 20° C. to 300° C., more preferably 80° C. to 250° C., and even more preferably 110° C. to 200° C. under ordinary pressure.

Specific examples of the solvent to be used in the dehydration reaction include a pyridine compound, a ketone compound, an ether compound, an ester compound and an alcohol, and a pyridine compound, a ketone compound, etc. are preferably used.

Examples of the pyridine compound, i.e., a compound having a pyridine skeleton serving as the solvent include 2-alkylpyridine, 3-alkylpyridine and 4-alkylpyridine such as 4-methylpyridine and pyridine. In particular, in the dehydration reaction in which pyridine may be generated as a by-product, when using the pyridine compound as the solvent with preferred conditions being set in advance, the step of removing pyridine as the main by-product is not required.

Further, examples of the ketone compound serving as the solvent include a cyclic ketone compound such as cyclopentanone and cyclohexane and acetone.

As the solvent for the dehydration reaction, it is preferred to use a solvent consisting of only one or more substances selected from the above-described compounds, but a mixed solvent further containing another compound may also be used.

(Conditions for Dehydration Reaction Including Contact Step)

As described above, the method for producing the aromatic nitrile compound has a contact step for bringing the aromatic amide compound into contact with the catalyst in the gas phase during the dehydration reaction.

In the contact step, the temperature at which the aromatic amide compound, etc. are brought into contact with the catalyst is preferably 170° C. or higher but lower than 300° C. The temperature is, for example, 180° C. or higher but lower than 290° C., or 190° C. or higher but lower than 280° C., more preferably 210° C. or higher but lower than 280° C., and even more preferably 220° C. or higher but lower than 260° C. It is considered that the temperature at which the aromatic amide compound, etc. are brought into contact with the catalyst is equal to, for example, the temperature of the inside of a reaction tube (reaction container) to which the catalyst is fixed.

Further, the time for bringing the aromatic amide compound into contact with the catalyst in the contact step, and in the case where an inert gas, a solvent, etc. are included together with the aromatic amide compound, the time for bringing a mixed gas of these gaseous compositions into contact with the catalyst are preferably 0.001 sec or more or 0.005 sec or more, for example, 0.01 sec or more, but less than 10 sec. The above-described time for contact with the catalyst is more preferably 0.1 sec or more but less than 5 sec, and even more preferably 0.5 sec or more but less than 2 sec.

Note that the time for contact with the catalyst is the average time during which the gas of the aromatic amide compound or the above-described mixed gas is passed through the catalyst layer, and it is calculated from: Time for contact with catalyst (sec)=Height of catalyst layer in reactor (cm)÷Linear velocity of gas in reactor (cm/sec).

In the contact step, the molar ratio between the flow rate of the aromatic amide compound and the flow rate of the gaseous composition is preferably 1:0 to 1:200, more preferably 1:1 to 1:100, and even more preferably 1:1 to 1:20.

The space velocity (SV) of the whole gas component in the contact step is preferably 1,000 to 50,000 ($h^{-1}$), more preferably 1,500 to 30,000 ($h^{-1}$), and even more preferably 2,000 to 25,000 ($h^{-1}$). Further, when performing the contact step under reduced pressure, the space velocity (SV) of the whole gas component is preferably 1,000 to 1,000,000 ($h^{-1}$), more preferably 1,500 to 700,000 ($h^{-1}$), and even more preferably 1,900 to 504,000 ($h^{-1}$).

Regarding conditions for the dehydration reaction, the pressure may be in the range of an elevated pressure (e.g., 506.5 (kPa)) to a reduced pressure (e.g., 0.1 (kPa)), but is not particularly limited thereto.

For example, the reaction pressure is 303.9 to 0.7 (kPa), preferably 202.6 to 0.9 (kPa), and more preferably 101.3 to 1.0 (kPa).

Further, it is preferred that the aromatic amide compound is dehydrated when it is in the form of liquid before vaporized. When using a molecular sieve as a dehydrating agent, the type and form thereof are not particularly limited, but for example, spherical or pellet-type molecular sieves 3A, 4A, 5A, etc. generally having high water absorbability can be used. For example, ZEOLUM manufactured by Tosoh Corporation can be suitably used.

(Example of by-Product in Dehydration Reaction)

It is considered that in the dehydration reaction of the aromatic amide compound, pyridine is by-produced via aromatic carboxylic acid due to decomposition of the aromatic amide compound as described above. However, almost no by-product such as pyridine shown in the above-described formula is generated in the reaction solution after the dehydration reaction using the contact step of the present invention.

<2. Method for Producing Carbonate Ester Using Aromatic Nitrile Compound>

By providing the contact step in the gas phase to the regeneration of the aromatic amide compound into the aromatic nitrile compound by means of the dehydration reaction, the reaction rate was successfully improved significantly to reduce the reaction time significantly. By this, it became possible to achieve a balance between the rate of regeneration of the aromatic amide compound into the aromatic nitrile compound by means of the dehydration reaction and the rate of synthesis of a carbonate ester from $CO_2$ and an alcohol using the aromatic nitrile compound, and it became possible to establish these reactions as a series of commercial processes. Accordingly, by applying this finding to a method for producing a carbonate ester, the present inventors successfully conceived the below-described method for producing a carbonate ester.

(First Reaction Step)

The first reaction step in the method for producing a carbonate ester of the present invention includes a reaction in which an alcohol is directly reacted with carbon dioxide in the presence of a solid catalyst containing, for example, $CeO_2$ (cerium oxide), etc. and the aromatic nitrile compound to produce the carbonate ester (carbonate ester production reaction).

In this step, when the alcohol is reacted with carbon dioxide, water is also produced in addition to the carbonate ester, and by a hydration reaction of the aromatic nitrile compound present in the reaction system and produced water, an aromatic amide compound is produced, and the produced water can be removed from the reaction system or reduced. By efficiently removing water from the reaction system in this way, the production of the carbonate ester can be promoted. For example, it is as shown in formula below.

(Alcohol)

In this regard, as the alcohol, any alcohol selected from one or more of a primary alcohol, a secondary alcohol and a tertiary alcohol can be used. For example, methanol, ethanol, 1-propanol, isopropanol, 1-butanol, 1-pentanol, 1-hexanol, 1-heptanol, 1-octanol, 1-nonanol, allyl alcohol, 2-methyl-1-propanol, cyclohexanemethanol, benzyl alcohol, ethylene glycol, 1,2-propanediol and 1,3-propanediol are preferably used because a high yield of a product and a high reaction rate are obtained. In these cases, carbonate esters produced are respectively dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonane carbonate, diallyl carbonate, di-2-methyl-propyl carbonate, dicyclohexanemethyl carbonate, dibenzyl carbonate, ethylene carbonate, 1,2-propylene carbonate and 1,3-propylene carbonate.

Further, in the first reaction step, an alcohol having 1 to 6 carbon atoms is preferably used, and an alcohol having 2 to 4 carbon atoms is more preferably used. In particular, when using the carbonate ester obtained as a raw material of diaryl carbonate, the carbon number of the alcohol is preferably adjusted within the above-described range.

Further, in the first reaction step, a monohydric alcohol or a dihydric alcohol is preferably used.

(Catalyst for Production of Carbonate Ester)

Further, in the first reaction step in the production of the carbonate ester, it is preferred to use one or both of $CeO_2$ and $ZrO_2$ as a solid catalyst. For example, it is preferred to use only $CeO_2$, only $ZrO_2$, a mixture of $CeO_2$ and $ZrO_2$, a solid solution or composite oxide of $CeO_2$ and $ZrO_2$ or the like, and it is particularly preferred to use only $CeO_2$. The mixing ratio between $CeO_2$ and $ZrO_2$ in the solid solution or composite oxide thereof is basically 50:50, but can be suitably changed.

In this regard, the catalyst to be used in the first reaction step may be in the form of either powder or a molded body, and in the case of the molded body, it may be any of a spherical type, a pellet type, a cylinder type, a ring type, a wheel type, a granular type, etc.

(Carbon Dioxide)

As carbon dioxide to be used in the present invention, not only carbon dioxide prepared as industrial gas, but also carbon dioxide separated and recovered from exhaust gas of plants producing various products, ironworks, power plants, etc. can be used.

(Solvent for Carbonate Ester Production Reaction)

In the carbonate ester production reaction, it is preferred to use a solvent having a boiling point higher than that of the amide compound to be produced. More preferably, the solvent in the carbonate ester production reaction contains at least one of dialkylbenzene, alkylnaphthalene and diphenylbenzene. Specific examples thereof include Barrel Process Oil B28AN and Barrel Process Oil B30 (manufactured by Matsumura Oil Co., Ltd.), each of which contains components including dialkylbenzene, alkylnaphthalene, diphenylbenzene, etc.

(Separation by Distillation)

After the reaction, a carbonate ester as the main product, an aromatic amide compound as a by-product, an unreacted aromatic nitrile compound, and a solid catalyst such as $CeO_2$ are separated by distillation, thereby recovering the products.

(Second Reaction Step)

Next, in the second reaction step in the present invention, the aromatic amide compound by-produced in the first reaction step is preferably separated from the system obtained after the carbonate ester production reaction, and then an aromatic nitrile compound is produced by means of a dehydration reaction. The second reaction step corresponds to the above-described method for producing the aromatic nitrile compound. Specifically, in the second reaction step for the production of the carbonate ester, the aromatic nitrile compound is produced from the aromatic amide compound according to the technique described in the column regarding the method for producing the aromatic nitrile compound above, thereby regenerating the aromatic nitrile compound. Accordingly, the details of the second reaction step are omitted.

(Reuse of Aromatic Nitrile Compound)

The aromatic nitrile compound regenerated in the second reaction step can be reused in the first reaction step (hydration reaction).

According to the present invention, as described above, by performing the dehydration reaction of the aromatic amide compound in the gas phase, the aromatic nitrile compound can be efficiently regenerated from the aromatic amide compound while suppressing the generation of a by-product. Moreover, by fixing the catalyst in a reaction tube, the step for subjecting the catalyst to solid-liquid separation is made unnecessary and the aromatic nitrile compound can be easily recovered. Thus, in the present invention, it is possible to selectively regenerate the aromatic nitrile compound from the aromatic amide compound, and to promote a series of reactions while separating the respective components only by distillation without solid-liquid separation of the catalyst. Accordingly, an efficient process, which will be described in detail later, can be realized.

<3. Apparatus for Producing Carbonate Ester>

Figure 1:
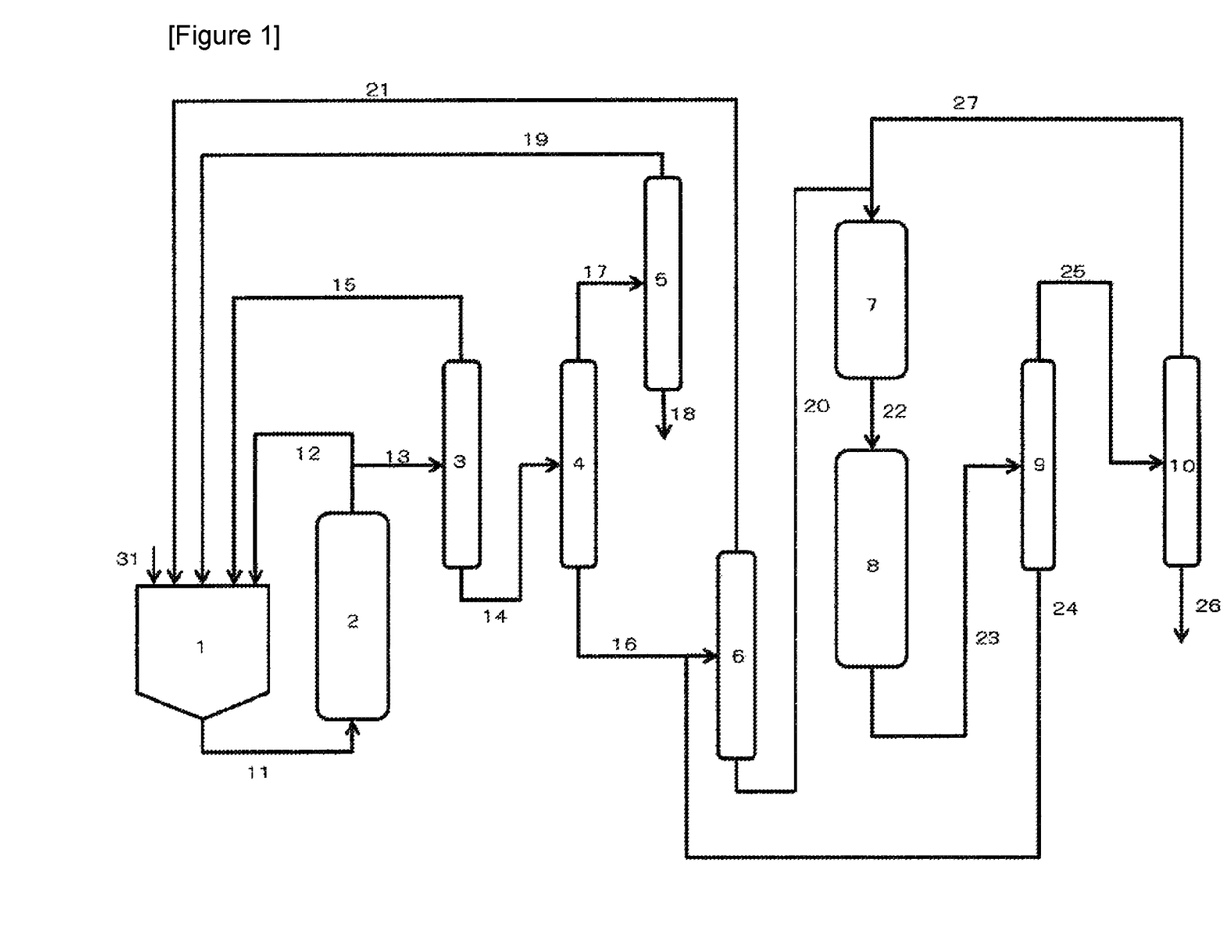
FIG. 1 shows an example of an apparatus for producing a carbonate ester.

Hereinafter, an apparatus for producing a carbonate ester to be used in the present invention will be described in detail by way of a specific example. FIG. 1 shows an example of a preferable apparatus.

(First Reaction Step)

In the first reaction step, raw materials, i.e., an alcohol (1-propanol (PrOH); liquid phase), 2-cyanopyridine (2-CP; liquid phase) and carbon dioxide ($CO_2$; liquid phase, it may be supplied via a booster pump) are continuously supplied to a buffer tank 1 using a raw material feed piping 31, a $CO_2$ recovery column top $CO_2$ transfer piping ($CO_2$ transfer piping at the top side of the $CO_2$ recovery column) 15, a carbonate ester recovery column top liquid transfer piping (liquid transfer piping at the top side of the carbonate ester recovery column) 19, and an amide separation column top liquid transfer piping (liquid transfer piping at the top side of the amide separation column) 21. This mixed solution of the raw materials is circulated between a fixed bed flow-type carbonate ester reactor 2 in which a solid catalyst (solid phase) consisting of one or both of $CeO_2$ and $ZrO_2$ is fixed to a support material (first reaction portion) and the buffer tank 1 via a first reaction solution circulation piping 11 and a second reaction solution circulation piping 12 using a pump (not shown), thereby synthesizing dipropyl carbonate (DPrC). The reaction solution containing DPrC is continuously withdrawn from the second reaction solution circulation piping 12 in the same amount as the amount of the raw materials supplied to the buffer tank 1, recovered using a piping 13, and delivered to a DPrC recovery step. PrOH and $CO_2$ are recovered from the reaction solution and transferred to the buffer tank 1 respectively via the carbonate ester recovery column top liquid transfer piping 19 and the $CO_2$ recovery column top $CO_2$ transfer piping 15, thereby reusing them. At the start of the reaction, new 2-cyanopyridine is used, but 2-cyanopyridine regenerated from 2-picolinamide is separated and purified in an amide separation column 6 and transferred to the buffer tank 1 via the amide separation column top liquid transfer piping 21, thereby reusing it.

As a direct synthesis apparatus for a carbonate ester using $CeO_2$, $ZrO_2$, etc. as a solid catalyst (carbonate ester reactor 2), any of flow reactors such as a batch reactor, a semi-batch reactor, a continuous tank reactor and a tube reactor may be used. When a catalyst is fixed to a reactor, it is not necessary to filter and separate the catalyst. For this reason, a fixed bed reactor is preferred.

(Reaction Solution Temperature)

The reaction solution temperature in the carbonate ester reactor 2 is preferably 50 to 300° C. When the reaction solution temperature is lower than 50° C., the reaction rate is low, the carbonate ester synthesis reaction and the hydration reaction with 2-cyanopyridine hardly progress, and the productivity of the carbonate ester tends to be low. When the reaction solution temperature is higher than 300° C., the reaction rate of each reaction is high, but the carbonate ester is easily decomposed or denatured and 2-picolinamide is easily reacted with an alcohol. For this reason, the yield of the carbonate ester tends to be low. The reaction solution temperature is more preferably 100 to 150° C. However, since it is considered that the ideal reaction solution temperature varies depending on the type and amount of the solid catalyst and the amount and ratio of the raw materials (alcohol and 2-cyanopyridine), it is desirable to suitably set optimum conditions. Since the preferred reaction solution temperature is 100 to 150° C., it is desirable to preheat the raw materials (alcohol and 2-cyanopyridine) with steam or the like on a stage before the carbonate ester reactor.

(Reaction Pressure)

The reaction pressure in the carbonate ester reactor 2 is preferably 0.1 to 20 MPa (absolute pressure). When the reaction pressure is lower than 0.1 MPa (absolute pressure), a decompression device is required. As a result, facilities are complicated and the cost is increased, and in addition, a power energy for reducing the pressure is required, resulting in decrease of the energy efficiency. When the reaction pressure is higher than 20 MPa, the hydration reaction with 2-cyanopyridine does not easily progress, resulting in decrease of the yield of the carbonate ester. In addition, a power energy for increasing the pressure is required, resulting in decrease of the energy efficiency. From the viewpoint of increasing the yield of the carbonate ester, the reaction pressure is more preferably 0.5 to 15 MPa (absolute pressure), and even more preferably 1.0 to 10 MPa (absolute pressure).

(Amount of 2-Cyanopyridine)

2-cyanopyridine to be used for the hydration reaction is preferably used in a molar quantity that is 0.1 to 5 times the theoretical molar quantity of water by-produced by the reaction of the alcohol and $CO_2$ as the raw materials, and it is desirably introduced into the reactor before the reaction. The molar quantity of 2-cyanopyridine is more desirably 0.2 to 3 times, and particularly desirably 0.3 to 1.5 times the theoretical molar quantity of water by-produced by the reaction of the alcohol and $CO_2$ as the raw materials. When the molar quantity of 2-cyanopyridine is too small, since the amount of 2-cyanopyridine contributing to the hydration reaction is small, the yield of the carbonate ester may be decreased. Meanwhile, when 2-cyanopyridine is introduced in an excess molar quantity relative to the alcohol as the raw material, the side reaction of 2-cyanopyridine is increased, and therefore it is undesirable. Since it is considered that the ideal amounts of the alcohol and 2-cyanopyridine relative to the solid catalyst vary depending on the type and amount of the solid catalyst, the type of the alcohol and the ratio between the alcohol and 2-cyanopyridine, it is desirable to suitably set optimum conditions.

(Separation of Reaction Products)

Preferably, the separation of reaction products is entirely performed by means of distillation. After the reaction in the carbonate ester reactor 2, a reaction solution 13 is transferred to a $CO_2$ recovery column 3. A mixture of PrOH, DPrC, 2-cyanopyridine and 2-picolinamide is recovered from the bottom of the $CO_2$ recovery column 3 via a $CO_2$ recovery column bottom liquid transfer piping 14, and $CO_2$ is recovered from the top of the $CO_2$ recovery column 3 via the $CO_2$ recovery column top $CO_2$ transfer piping 15. The recovered $CO_2$ is transferred to the buffer tank 1 and recycled in the reaction in the carbonate ester reactor 2.

The mixture recovered from the $CO_2$ recovery column 3 is transferred to a dehydrating agent separation column 4 via the $CO_2$ recovery column bottom liquid transfer piping 14. A mixture of 2-cyanopyridine and 2-picolinamide is recovered from the bottom of the dehydrating agent separation column 4 via a dehydrating agent separation column bottom liquid transfer piping 16, and PrOH and DPrC are recovered from the top of the dehydrating agent separation column 4 via a dehydrating agent separation column top liquid transfer piping 17.

The mixture recovered from the bottom of the dehydrating agent separation column 4 is transferred to the amide separation column 6 via the dehydrating agent separation column bottom liquid transfer piping 16. 2-picolinamide (20) is recovered from the bottom of the amide separation column 6, and 2-cyanopyridine is recovered from the top of the amide separation column 6. The recovered 2-cyanopyridine is transferred to the buffer tank 1 via the amide separation column top liquid transfer piping 21 and recycled in the reaction in the carbonate ester reactor 2.

PrOH and DPrC recovered from the top of the dehydrating agent separation column 4 is transferred to a carbonate ester recovery column 5 via the dehydrating agent separation column top liquid transfer piping 17. DPrC is recovered from the bottom of the carbonate ester recovery column 5 via a carbonate ester recovery column bottom liquid transfer piping 18, and PrOH is recovered from the top of the carbonate ester recovery column 5 via the carbonate ester recovery column top liquid transfer piping 19. The recovered PrOH is transferred to the buffer tank 1 and recycled in the reaction in the carbonate ester reactor 2.

(Second Reaction Step)

In the second reaction step, 2-cyanopyridine is produced by a dehydration reaction of 2-picolinamide in a nitrile regeneration gas phase reactor 8.

2-picolinamide recovered from the amide separation column 6 is transferred to a vaporizer 7 via an amide separation column bottom liquid transfer piping 20. Preferably, it is mixed with an inert gas that is nitrogen or the like, the mixture is heated to a temperature near the boiling point of amide to provide a gas or a mixed gas consisting of gas and droplets, and it is transferred to the nitrile regeneration gas phase reactor 8 via a vaporizer-nitrile regeneration gas phase reactor connection piping 22. The form of the vaporizer 7 for vaporizing the amide compound, etc. is not particularly limited, and any of an ejector type vaporizer, a contact type vaporizer, a bubbling device, etc. may be used.

In the apparatus for producing a nitrile compound to be used in the present invention (nitrile regeneration gas phase reactor 8), 2-picolinamide, and preferably, an inert gas that is nitrogen or the like, etc. are brought into contact with a catalyst containing a carried basic metal oxide in the gas phase to cause a dehydration reaction of 2-picolinamide. By this dehydration reaction, 2-cyanopyridine is produced. When transferring the amide compound, for the purpose of preventing the trouble of closure, the amide compound can be dissolved in a transfer solvent to transfer the liquid. When using an amide transfer solvent, it is preferred that the solvent is also vaporized together with amide to perform a nitrile regeneration gas phase reaction. In this case, a solvent vapor can be used instead of the inert gas.

The form of the nitrile regeneration gas phase reactor 8 is not particularly limited. It is preferred to use a gas phase reaction in which the amide compound in the form of gas or mist is flowed through the catalyst layer together with the inert gas and the like, and a gas phase reaction apparatus with a fixed bed, fluidized bed or the like can be applied thereto.

Thus, for efficiently promoting the dehydration reaction by bringing 2-picolinamide into contact with the catalyst, etc. in the gas phase, the above-described various reaction conditions related to the dehydration reaction or reaction conditions described in the Examples below are appropriately employed.

The mixed gas containing 2-cyanopyridine is transferred from the gas phase reactor 8 to an $H_2O$ separation apparatus 9 via a gas phase reaction product transfer piping 23. Water and nitrogen gas are separated from the mixed gas in the $H_2O$ separation apparatus 9, and 2-cyanopyridine and 2-picolinamide recovered are transferred from the $H_2O$ separation apparatus 9 to the amide separation column 6 via a high boiling transfer piping 24. Further, 2-picolinamide is recovered from the bottom of the amide separation column 6 via the amide separation column bottom liquid transfer piping 20 and transferred to the vaporizer 7, and 2-cyanopyridine is recovered from the top of the amide separation column 6. 2-cyanopyridine recovered is transferred to the buffer tank 1 via the amide separation column top liquid transfer piping 21 and recycled in the reaction in the carbonate ester reactor 2.

Further, nitrogen gas and water separated in the $H_2O$ separation apparatus 9 are transferred to an $N_2$ recovery apparatus 10 via a light boiling transfer piping 25, and water is separated in the $N_2$ recovery apparatus 10 to recover nitrogen gas. Water separated in the $N_2$ recovery apparatus 10 is transferred to the outside of the carbonate ester apparatus via an $N_2$ recovery apparatus water transfer piping 26. Nitrogen gas recovered in the $N_2$ recovery apparatus 10 is transferred to the vaporizer 7 via an $N_2$ recovery apparatus $N_2$ transfer piping 27, and it can be used in the gas phase reaction. In the case of using an amide compound transfer solvent, a step of recovering the solvent is provided separately, thereby reusing the solvent for transferring the amide compound. The form of each of the $H_2O$ separation apparatus 9 and the $N_2$ recovery apparatus 10 is not particularly limited, and any of a cooling system, a membrane separation apparatus, etc. may be used.

As described above, in the present invention, dehydration of the amide compound can be promoted by the contact step in the gas phase, and in addition, the reaction product and compounds to be reused can be separated by distillation or the like without solid-liquid separation. For this reason, according to the present invention, it is possible to efficiently produce a carbonate ester in a smaller number of production steps while simplifying apparatuses.

EXAMPLES

Hereinafter, the present invention will be more specifically described by way of examples, but the present invention is not limited thereto. Firstly, examples and comparative examples of the method for producing cyanopyridine will be described below.

Example 1

$SiO_2$ as a carrier (manufactured by Fuji Silysia Chemical Ltd., CARiACT, Q-6 (carrier diameter: 0.075 to 0.15 mm)) was pre-baked at 700° C. for about 1 hour. After that, for carrying Cs as an alkali metal, an aqueous solution was prepared using $Cs_2CO_3$ (manufactured by Wako Pure Chemical Industries, Ltd.) such that the final amount of Cs metal to be carried would be 0.5 mmol/g, and $SiO_2$ was impregnated with the aqueous solution. After that, the obtained material was dried at 110° C. for about 6 hours and then baked at 500° C. for about 3 hours, thereby obtaining a $Cs_2O/SiO_2$ catalyst.

Figure 2:
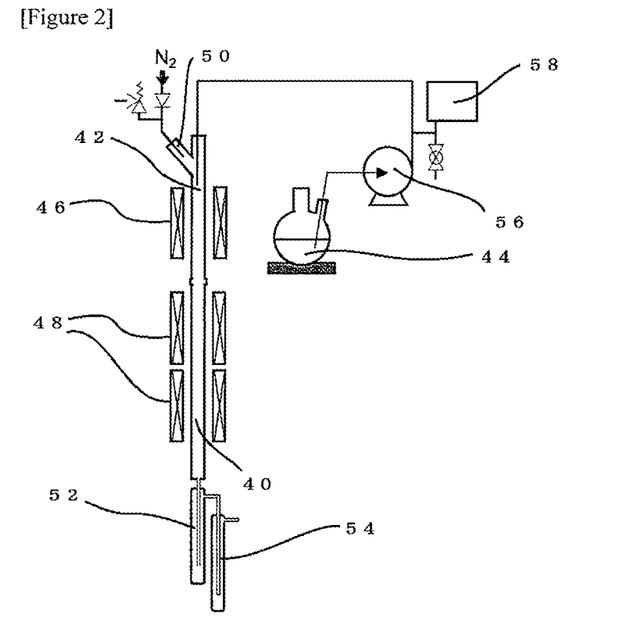
FIG. 2 schematically shows an apparatus for producing cyanopyridine which was used in working examples in which cyanopyridine was produced under elevated pressure or ordinary pressure.

A reaction tube 40 made of SUS 304 having an inner diameter of 10.7 mm and a length of 30 cm was filled with the catalyst produced by the above-described production method (see FIG. 2). Further, immediately above the reaction tube 40, a vaporizing chamber 42 made of SUS 304 having an inner diameter of 10.7 mm and a length of 30 cm filled with Raschig ring was provided.

10 g of 2-picolinamide (2-PA) was dissolved in 4-methylpyridine serving as a transfer solvent (90 g), and the mixture was put into a raw material container 44. The raw material container 44 was placed on a precision balance, a suction tube with a filter was dropped into the raw material solution, and the balance was stabilized.

Nitrogen was flowed through the vaporizing chamber 42 connected to the raw material container 44, and the reaction tube 40 at a flow rate of 1000 mL/min, and the vaporizing chamber 42 and the reaction tube 40 were heated to 230° C. respectively with mantle heaters 46 and 48. Further, a piping 50 for feeding nitrogen and a piping at the exit side of the reaction tube 40 were kept at 150° C. For recovering a reaction product, a water cooling trap container 52 was located at the first stage, a dry ice/methanol cooling trap container 54 was located at the second stage, and a liquid nitrogen cooling trap container (not shown) was located at the final stage.

After the temperature of the catalyst layer became stable, a plunger pump 56 was started, and a reaction was performed for the time described in the column of the catalyst contact time in the table below. During the reaction, excessive pressurization was prevented by a pressure limiter 58 so that the pressure in the reaction system of the cyanopyridine production apparatus shown in FIG. 2 did not exceed 506.5 (kPa).

The conditions for the above-described contact reaction (dehydration reaction) were as shown in Table 1. After the reaction was completed, the obtained reaction product was recovered and analyzed with GC-FID.

The analysis conditions for the results of the contact reaction (dehydration reaction) were as shown below.
[Analysis Conditions] (GC-FID)
Shimadzu GC-2014, column: TC-17 (length: 30 m, inner diameter: 0.25 mmID, thickness of liquid phase: 0.25 μm)
Temperature of vaporizing chamber: 250° C., Detector: 260° C., Carrier He: 175 kPa, Flow rate of column: 2.5 mL/min, Split ratio: 50

Temperature program: [kept at 70° C. for 5 min]→[elevated to 190° C., 12° C./min]→[kept at 190° C. for 5 min]→[elevated to 250° C.,12° C./min]→[kept at 250° C. for 10 min]

[24-hour yield per 1 g of catalyst(mmol/24 hr·g)]=(Recovery amount of product after 24-hour reaction(mmol))/(Amount of catalyst(g))

[Space velocity: $SV(hr^{-1})$]=(Amount of gas passed through catalyst layer($L \cdot hr^{-1}$))/(Amount of catalyst(L)) Amount of gas: the sum of volumes of gases of nitrogen,2-PA and solvent($L \cdot hr^{-1}$)

[Catalyst filling height(height of catalyst layer in reactor)]: height of catalyst filled in reaction tube(cm)

[Catalyst contact time (sec)]=[Catalyst filling height (cm)]/[Linear velocity (linear velocity of gas in reactor)(cm/sec)]

[Carrier Diameter of Catalyst]

The value of the carrier diameter of the catalyst is measured based on the sieving method: Test sieving—General requirements defined in JIS Z 8815.

Examples 2-15

In Example 2 or later, a reaction was performed in a manner similar to that in Example 1, except that the conditions were changed as shown in Table 1. The results are shown in Table 1.

In each of the Examples and Comparative Examples, the active component of the catalyst was $Cs_2O$; CARIACT Q-6 (the main component is $SiO_2$) manufactured by Fuji Silysia Chemical Ltd. was used as the carrier; and the amount of an active metal carried by the catalyst (carrying amount in metal conversion of the active species based on the total catalyst weight) was 0.5 mmol/g. Further, in each of the Examples and Comparative Examples, 2-picolinamide (2-PA) was used as the aromatic amide compound.

Example 16

Unlike Examples 1-15, in Example 16, the contact reaction (dehydration reaction) of the aromatic amide compound was performed under reduced pressure. Specifically, it was performed as described below.

100 g of 2-picolinamide (2-PA) was dissolved in cyclopentanone serving as a transfer solvent (900 g), and the mixture was put into a raw material container.

Figure 3:
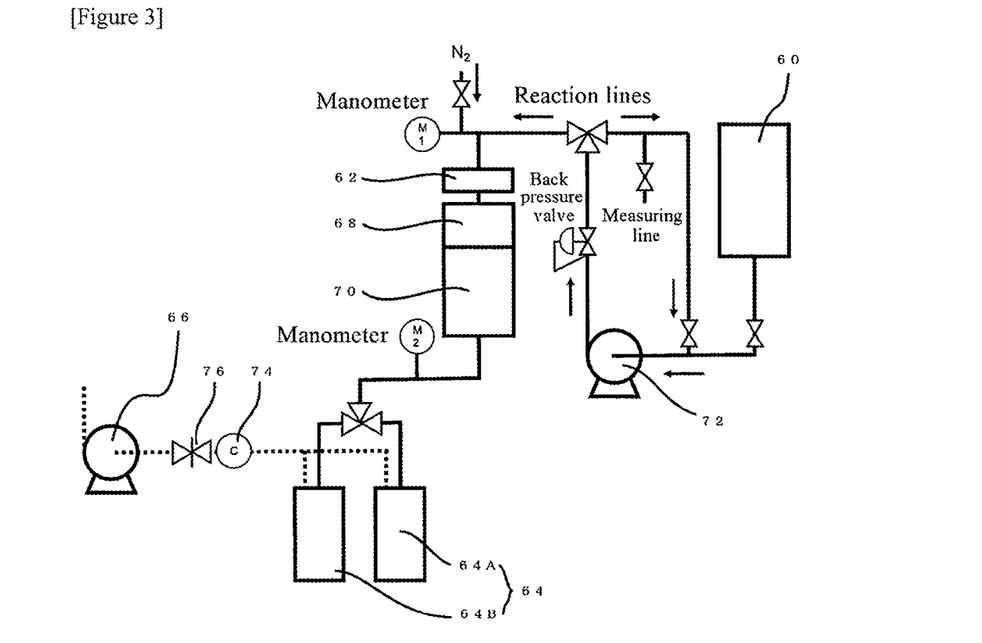
FIG. 3 schematically shows an apparatus for producing cyanopyridine which was used in working examples in which cyanopyridine was produced under reduced pressure.

Nitrogen was flowed through a reaction line (from an ejector 62 to a trap 64 shown in FIG. 3) connected to the raw material container 60 at a flow rate of 1000 mL/min. After the feed of nitrogen was stopped, a vacuum pump 66 was connected to the trap 64, and the pressure in the reaction system was reduced to 0.5 kPa. A vaporizer 68 and a reactor 70 were heated to 220° C. respectively with electric furnaces (not shown). Further, a piping at the exit side of the reaction line was heated to 150° C. using a ribbon heater (not shown). For recovering a reaction product, a dry ice/methanol cooling trap container 64 was located (a first fraction trap 64A and a recovery trap 64B in FIG. 3), and next to that, a liquid nitrogen cooling trap container (not shown) was located.

After the temperature of the catalyst layer (not shown) placed in the reactor 70 became stable, a plunger pump 72 was started, and a reaction was performed. For 90 minutes from the time when the inside of the catalyst layer reached the steady state, a reaction product was recovered with the recovery trap 64B. During the reaction, the pressure in the reaction system of the cyanopyridine production apparatus shown in FIG. 3 was controlled with a pressure reduction controller 74 and a needle valve 76. Note that until the inside of the catalyst layer reached the steady state, and after the reaction product was recovered with the recovery trap 64B after the inside of the catalyst layer reached the steady state, the reaction product was recovered with the first fraction trap 64A.

The conditions for the above-described contact reaction (dehydration reaction) were as shown in Table 1. After the reaction was completed, the obtained reaction product was recovered and analyzed with GC-FID.

Examples 17-21

In Example 17 or later, a reaction was performed in a manner similar to that in Example 16, except that the conditions were changed as shown in Table 1.

The results of Examples 1-21 are shown in Table 1 below.

TABLE 1

| Examples | Carrier diameter mm | Catalyst Amount of catalyst g | Catalyst filling height cm | Transfer solvent | Flow rate of N₂ mL/min | Molar flow rate 2-Pa mmol/h | Transfer solvent mmol/h | N₂ mmol/h | Space velocity SV h-1 | Linear velocity cm/sec | Catalyst contact time sec | Temperature of vaporizing chamber ° C. | Temperature of reaction tube ° C. | Reaction pressure kPa | 2-CP mmol/h | Pyridine mmol/h | 24-hour yield per 1 g of catalyst 2-CP mmol/g · 24 h | Pyridine mmol/g · 24 h |
|---|---|---|---|---|---|---|---|---|---|---|---|---|---|---|---|---|---|---|
| 1 | 0.075 to 0.15 | 1.7990 | 3.89 | 4-methyl-pyridine | 1000 | 33.8 | 398 | 2679 | 19905 | 21.5 | 0.18 | 230 | 225 | 303.9 | 9.6 | 0.0 | 128 | 0.00 |
| 2 | 0.075 to 0.15 | 1.7990 | 3.89 | 4-methyl-pyridine | 1000 | 33.8 | 399 | 2679 | 19911 | 21.5 | 0.18 | 250 | 247 | 303.9 | 18.7 | 0.0 | 250 | 0.00 |
| 3 | 0.075 to 0.15 | 1.7990 | 3.89 | 4-methyl-pyridine | 1000 | 78.9 | 414 | 2679 | 20300 | 21.9 | 0.18 | 230 | 225 | 303.9 | 16.7 | 0.0 | 223 | 0.00 |
| 4 | 0.075 to 0.15 | 1.7990 | 3.89 | 4-methyl-pyridine | 1000 | 32.6 | 171 | 2893 | 19820 | 21.4 | 0.18 | 230 | 225 | 303.9 | 10.9 | 0.0 | 145 | 0.00 |
| 5 | 1.7 to 4.0 | 9.0020 | 15.57 | 4-methyl-pyridine | 1000 | 38.0 | 447 | 2679 | 5062 | 21.9 | 0.71 | 230 | 225 | 101.3 | 10.7 | 0.0 | 28.6 | 0.00 |
| 6 | 1.7 to 4.0 | 9.0020 | 15.57 | — | 1000 | 19.5 | 0 | 2679 | 4317 | 18.7 | 0.83 | 250 | 247 | 101.3 | 11.5 | 0.0 | 30.8 | 0.00 |
| 7 | 1.7 to 4.0 | 9.0020 | 15.57 | — | 1000 | 90.1 | 0 | 2679 | 4430 | 19.2 | 0.81 | 250 | 248 | 101.3 | 23.1 | 0.0 | 61.5 | 0.00 |
| 8 | 1.7 to 4.0 | 2.1500 | 3.89 | Cyclo-pentanone | 250 | 697 | 954 | 670 | 14851 | 16.1 | 0.24 | 250 | 243 | 101.3 | 22.2 | 0.0 | 248.3 | 0.00 |
| 9 | 1.7 to 4.0 | 2.1500 | 3.89 | Cyclo-pentanone | 0 | 378 | 337 | 0 | 4576 | 4.9 | 0.79 | 250 | 245 | 101.3 | 9.5 | 0.0 | 106.3 | 0.00 |
| 10 | 1.7 to 4.0 | 2.1500 | 3.89 | Cyclo-pentanone | 0 | 93 | 68 | 0 | 1028 | 1.1 | 3.50 | 250 | 245 | 101.3 | 2.9 | 3.6 | 31.8 | 39.96 |
| 11 | 1.7 to 4.0 | 2.1500 | 3.89 | Cyclo-pentanone | 0 | 61 | 629 | 0 | 4417 | 4.8 | 0.82 | 265 | 259 | 101.3 | 1.7 | 0.0 | 18.7 | 0.00 |
| 12 | 1.7 to 4.0 | 2.1500 | 3.89 | Cyclo-pentanone | 225 | 45 | 60 | 603 | 4530 | 4.9 | 0.79 | 255 | 249 | 101.3 | 0.6 | 0.0 | 6.3 | 0.00 |
| 13 | 1.7 to 4.0 | 9.0020 | 15.57 | Cyclo-pentanone | 1000 | 26 | 34 | 2679 | 4382 | 19.0 | 0.82 | 250 | 247 | 101.3 | 13.4 | 0.0 | 35.7 | 0.00 |
| 14 | 1.7 to 4.0 | 9.0020 | 15.57 | Cyclo-pentanone | 1000 | 65 | 85 | 2679 | 4527 | 19.6 | 0.80 | 250 | 246 | 101.3 | 23.6 | 0.0 | 63.0 | 0.00 |
| 15 | 1.7 to 4.0 | 9.0020 | 15.57 | Cyclo-pentanone | 1000 | 178 | 238 | 2679 | 4951 | 21.4 | 0.73 | 250 | 246 | 101.3 | 38.7 | 0.0 | 103.1 | 0.00 |
| 16 | 1.7 to 4.0 | 250.17 | 32.5 | Cyclo-pentanone | 0 | 97 | 1191 | 0 | 8133 | 73 | 0.44 | 188 | 224 | 1.4 | 58.5 | 0.7 | 5.6 | 0.066 |
| 17 | 1.7 to 4.0 | 250.17 | 32.5 | Cyclo-pentanone | 0 | 88 | 1117 | 0 | 9835 | 89 | 0.37 | 168 | 186 | 1.0 | 18.9 | 0.1 | 1.8 | 0.007 |

TABLE 1-continued

| Examples | Carrier diameter mm | Catalyst Amount of catalyst g | Catalyst filling height cm | Transfer solvent | Flow rate of N₂ mL/min | Molar flow rate 2-Pa mmol/h | Molar flow rate Transfer solvent mmol/h | Molar flow rate N₂ mmol/h | Space velocity SV h-1 | Linear velocity cm/sec | Catalyst contact time sec | Temperature of vaporizing chamber °C. | Temperature of reaction tube °C. | Reaction pressure kPa | 2-CP mmol/h | Pyridine mmol/h | 24-hour yield per 1 g of catalyst 2-CP mmol/ g · 24 h | 24-hour yield per 1 g of catalyst Pyridine mmol/ g · 24 h |
|---|---|---|---|---|---|---|---|---|---|---|---|---|---|---|---|---|---|---|
| 18 | 1.7 to 4.0 | 250.17 | 32.5 | Cyclopentanone | 0 | 119 | 470 | 0 | 1923 | 17 | 1.87 | 165 | 185 | 2.1 | 21.8 | 1.1 | 2.1 | 0.109 |
| 19 | 1.7 to 4.0 | 250.17 | 32.5 | Cyclopentanone | 0 | 81 | 127 | 0 | 2404 | 22 | 1.50 | 166 | 187 | 0.7 | 10.9 | 0.4 | 1.0 | 0.039 |
| 20 | 0.075 to 0.15 | 5.04 | 0.7 | Cyclopentanone | 0 | 88 | 1118 | 0 | 503741 | 95 | 0.01 | 186 | 220 | 1.0 | 6.4 | 0 | 30.7 | 0.00 |
| 21 | 0.075 to 0.15 | 15.3 | 2.1 | Cyclopentanone | 0 | 89 | 1137 | 0 | 189040 | 109 | 0.02 | 185 | 225 | 0.9 | 10.7 | 0 | 16.7 | 0.00 |

Comparative Examples 1-9

In Comparative Examples 1-9, a solvent was used for removing water produced by the reaction to the outside of the reaction system, and a dehydration reaction was performed in a liquid phase.

Comparative Example 1

$SiO_2$ as a carrier (manufactured by Fuji Silysia Chemical Ltd., CARiACT, Q-6 (carrier diameter: 0.075 to 0.15 mm)) was pre-baked at 700° C. for about 1 hour. After that, for carrying Cs as an alkali metal, an aqueous solution was prepared using $Cs_2CO_3$ (manufactured by Wako Pure Chemical Industries, Ltd.) such that the final amount of Cs metal to be carried would be 0.5 mmol/g, and $SiO_2$ was impregnated with the aqueous solution. After that, the obtained material was dried at 110° C. for about 6 hours and then baked at 500° C. for about 3 hours, thereby obtaining a $Cs_2O/SiO_2$ catalyst.

Next, a three-necked round-bottom flask was used as a reactor, and a magnetic stirring bar, the above-described $Cs_2O/SiO_2$ catalyst, 2-picolinamide (manufactured by Tokyo Chemical Industry Co., Ltd.) and 1,3-dimethoxybenzene (manufactured by Tokyo Chemical Industry Co., Ltd.) were introduced into the reactor.

Further, a thermometer and an air cooling tube containing 10 g of molecular sieve 4A were attached to the reactor, and a Liebig condenser is attached to the upper end of the air cooling tube to provide a reaction apparatus.

Subsequently, the reaction solution was heated under ordinary pressure and kept in a boiled state, and by-product water was adsorbed to the molecular sieve without being returned to the reactor to perform dehydration, thereby performing the reaction.

The reaction was started when the reaction solution started to boil, and the reaction was performed for 24 hours.

After the reaction, the temperature was decreased to room temperature. The reaction solution was sampled and diluted two-fold with ethanol, and 1-hexanol was added thereto as an internal standard substance. The resultant substance was subjected to qualitative analysis with GC-MS (gas chromatograph-mass spectrometer) and to quantitative analysis with GC-FID.

Comparative Examples 2-7

In Comparative Examples 2-7, a reaction was performed in a manner similar to that in Comparative Example 1, except that the conditions were changed as shown in Table 2.

Comparative Examples 8-9

In Comparative Examples 8-9, the conditions were changed as shown in Table 2, and in addition, the apparatus configuration and reaction conditions were changed as described below, thereby performing a reaction.

$SiO_2$ as a carrier (manufactured by Fuji Silysia Chemical Ltd., CARiACT, Q-6 (carrier diameter: 0.075 to 0.15 mm)) was sized to 100 mesh or less and pre-baked at 700° C. for about 1 hour. After that, for carrying Cs as an alkali metal, an aqueous solution was prepared using $Cs_2CO_3$ (manufactured by Wako Pure Chemical Industries, Ltd.) such that the final amount of Cs metal to be carried would be 0.5 mmol/g, and $SiO_2$ was impregnated with the aqueous solution. After that, the obtained material was dried at 110° C. for about 6 hours and then baked at 500° C. for about 3 hours, thereby obtaining a $Cs_2O/SiO_2$ catalyst.

Next, a three-necked round-bottom flask was used as a reactor, and a magnetic stirring bar, the above-described $Cs_2O/SiO_2$ catalyst, 2-picolinamide (manufactured by Tokyo Chemical Industry Co., Ltd.) and diphenyl ether (manufactured by Tokyo Chemical Industry Co., Ltd.) were introduced into the reactor.

Further, a thermometer and a first air cooling tube as a distillation column were attached to the reactor, a distilling head equipped with a thermometer was attached to the upper end of the first air cooling tube, and a second air cooling tube, a receiver and a vacuum pump were connected to the distilling head to provide a reaction distillation apparatus. Note that a ribbon heater was wound around the first air cooling tube for adjusting the temperature. Further, a cooling trap was cooled with liquid nitrogen for recovering vaporized pyridine.

Subsequently, the pressure in the reaction distillation apparatus was reduced to 13.3 kPa (100 Torr) using the vacuum pump. The first air cooling tube was heated to 60° C., which was higher than the boiling point of water and lower than the boiling point of diphenyl ether under the reaction pressure. The reaction solution was maintained in a boiled state at 184° C., which was equal to or higher than the boiling point of diphenyl ether and lower than the boiling point of 2-picolinamide under the reaction pressure. By adjusting the temperature in this manner, partially vaporized diphenyl ether in the reaction system was cooled in the first air cooling tube and returned to the reactor while the by-product water was distilled away to the outside of the system without being returned to the reactor, thereby performing the reaction.

The reaction was started when the reaction solution started to boil, and the reaction was performed for 24 hours.

After the reaction, the temperature was decreased to room temperature. The reaction solution was sampled and diluted two-fold with ethanol, and 1-hexanol was added thereto as an internal standard substance. The resultant substance was subjected to qualitative analysis with GC-MS (gas chromatograph-mass spectrometer) and to quantitative analysis with GC-FID.

The results of Comparative Examples 1-9 are shown in Table 2 below.

TABLE 2

| Comparative Examples | Carrier diameter mm | Amount of catalyst g | Liquid phase solvent | Amount of solvent mL | Amount of substrate mmol | Temperature of reaction solution ° C. | Reaction pressure kPa | 2-CP mmol | Pyridine mmol | 24-hour yield per 1 g of catalyst 2-CP mmol/ g · 24 h | Pyridine mmol/ g · 24 h |
|---|---|---|---|---|---|---|---|---|---|---|---|
| 1 | 0.075 to 0.15 | 0.31 | 1,3-dimethoxybenzene | 60 | 15.0 | 215 (boiled) | 101.3 | 10.4 | 0.13 | 33.5 | 0.42 |
| 2 | 0.075 to 0.15 | 0.31 | 1,2,3,4-tetrahydronaphthalene | 60 | 15.0 | 210 (boiled) | 101.3 | 8.47 | 0.10 | 27.3 | 0.31 |

TABLE 2-continued

| Comparative Examples | Carrier diameter mm | Amount of catalyst g | Liquid phase solvent | Amount of solvent mL | Amount of substrate mmol | Temperature of reaction solution °C | Reaction pressure kPa | 2-CP mmol | Pyridine mmol | 24-hour yield per 1 g of catalyst | |
|---|---|---|---|---|---|---|---|---|---|---|---|
| | | | | | | | | | | 2-CP mmol/ g · 24 h | Pyridine mmol/ g · 24 h |
| 3 | 0.075 to 0.15 | 0.31 | 1,2-dimethoxybenzene | 60 | 15.0 | 210 (boiled) | 101.3 | 8.18 | 0.07 | 26.4 | 0.22 |
| 4 | 0.075 to 0.15 | 0.31 | 1,3,5-trimethoxybenzene | 60 | 15.0 | 203 (not boiled) | 101.3 | 2.27 | 0.15 | 7.32 | 0.49 |
| 5 | 0.075 to 0.15 | 0.31 | 1,3,5-trimethylbenzene | 60 | 15.0 | 165 (boiled) | 101.3 | 2.70 | 0.00 | 8.7 | 0.00 |
| 6 | 1.7 to 4.0 | 0.31 | 1,3,5-trimethylbenzene | 60 | 15.0 | 165 (boiled) | 101.3 | 0.29 | 0.00 | 0.9 | 0.00 |
| 7 | 1.7 to 4.0 | 3.0 | 1,3,5-trimethylbenzene | 60 | 15.0 | 165 (boiled) | 101.3 | 5.00 | 0.015 | 1.67 | 0.005 |
| 8 | 0.075 to 0.15 | 1.0 | Diphenyl ether | 200 | 48.0 | 181 (boiled) | 13.3 | 23.4 | 0.14 | 23.4 | 0.14 |
| 9 | 1.7 to 4.0 | 1.0 | Diphenyl ether | 200 | 48.0 | 181 (boiled) | 13.3 | 2.47 | 0.015 | 2.47 | 0.015 |

With reference to the attached drawings, the preferred embodiments of the present invention are described in detail above, but the present invention is not limited to the examples. Those skilled in the art of the present invention would obviously conceive any of various altered or modified examples within the scope of the technical idea recited in the claims, and it is understood that such altered or modified examples are duly encompassed in the technical scope of the present invention.

DESCRIPTION OF REFERENCE NUMERALS 1 buffer tank ($CO_2$, PrOH, DPrC, 2-CP, 2-PA)
2 carbonate ester reactor ($CO_2$, PrOH, DPrC, 2-CP, 2-PA, fixed catalyst)
3 $CO_2$ recovery column ($CO_2$, PrOH, DPrC, 2-CP, 2-PA)
4 dehydrating agent separation column (PrOH, DPrC, 2-CP, 2-PA)
5 carbonate ester recovery column (PrOH, DPrC)
6 amide separation column (2-CP, 2-PA)
7 vaporizer ($N_2$, 2-PA)
8 nitrile regeneration gas phase reactor ($N_2$, $H_2O$, 2-CP, 2-PA, catalyst)
9 $H_2O$ separation apparatus ($N_2$, $H_2O$, 2-CP, 2-PA)
10 $N_2$ recovery apparatus ($N_2$, $H_2O$)
11 first reaction solution circulation piping ($CO_2$, PrOH, DPrC, 2-CP, 2-PA)
12 second reaction solution circulation piping ($CO_2$, PrOH, DPrC, 2-CP, 2-PA)
13 reaction solution withdrawing piping ($CO_2$, PrOH, DPrC, 2-CP, 2-PA)
14 $CO_2$ recovery column bottom liquid transfer piping (PrOH, DPrC, 2-CP, 2-PA)
15 $CO_2$ recovery column top $CO_2$ transfer piping ($CO_2$)
16 dehydrating agent separation column bottom liquid transfer piping (2-CP, 2-PA)
17 dehydrating agent separation column top liquid transfer piping (PrOH, DPrC)
18 carbonate ester recovery column bottom liquid transfer piping (DPrC)
19 carbonate ester recovery column top liquid transfer piping (PrOH)
20 amide separation column bottom liquid transfer piping (2-PA)
21 amide separation column top liquid transfer piping (2-CP)
22 vaporizer-nitrile regeneration gas phase reactor connection piping ($N_2$, 2-PA)
23 gas phase reaction product transfer piping ($N_2$, $H_2O$, 2-CP, 2-PA)
24 $H_2O$ separation apparatus high boiling transfer piping (2-CP, 2-PA)
25 $H_2O$ separation apparatus light boiling transfer piping ($N_2$, $H_2O$)
26 $N_2$ recovery apparatus water transfer piping ($H_2O$)
27 $N_2$ recovery apparatus $N_2$ transfer piping ($N_2$)
31 raw material feed piping ($CO_2$, PrOH)
40 reaction tube
42 vaporizing chamber
44 raw material container
46, 48 mantle heater
50 nitrogen gas feed piping
52 water cooling trap container
54 dry ice/methanol cooling trap container
56 plunger pump
58 pressure limiter
60 raw material container
62 ejector
64 trap
64A first fraction trap
64B recovery trap
66 vacuum pump
68 vaporizer
70 reactor
72 plunger pump
74 pressure reduction controller
76 needle valve

The invention claimed is:

1. A method for producing a carbonate ester, which has:
a first reaction that includes: a carbonate ester production reaction in which an alcohol is reacted with carbon dioxide in the presence of an aromatic nitrile compound to produce the carbonate ester and water, and a hydration reaction in which the aromatic nitrile compound is hydrated with the produced water to produce an aromatic amide compound; and
a second reaction in which the aromatic amide compound is separated from the reaction system of the first reaction and then the aromatic amide compound is regenerated into an aromatic nitrile compound by means of a dehydration reaction for dehydrating the aromatic amide compound, the dehydration reaction comprising contacting the aromatic amide compound with a catalyst in a gas phase, wherein at least a part of the aromatic nitrile compound regenerated in the second reaction is used in the first reaction, wherein a first catalyst which is cerium oxide is used in the carbonate ester production reaction, wherein a second catalyst which comprises an alkali metal is used in the dehydration reaction and the second catalyst comprises an oxide of an alkali metal selected from the group consisting of K, Li, Na, Rb, and Cs, and wherein the time for bringing the aromatic amide compound into contact with the second catalyst in the contacting, is 0.001 sec or more and less than 10 sec.

2. The method for producing a carbonate ester according to claim 1, wherein in the second reaction, an aromatic nitrile compound is produced from an aromatic amide compound according to a method for producing an aromatic nitrile compound to regenerate the aromatic nitrile compound, the method for producing an aromatic nitrile compound comprising a dehydration reaction, wherein an aromatic amide compound is dehydrated, the method comprising contacting the aromatic amide compound with a catalyst in a gas phase during the dehydration reaction, wherein the catalyst includes an alkali metal.

3. The method for producing a carbonate ester according to claim 1, wherein the second catalyst is an oxide of an alkali metal selected from the group consisting of K, Li, Na, Rb, and Cs.

4. The method for producing a carbonate ester according to claim 1, wherein the alcohol includes an alcohol having 1 to 6 carbon atoms.

5. The method for producing a carbonate ester according to claim 1, wherein the aromatic amide compound in the form of gas or mist is flowed through a catalyst layer during the contacting.

* * * * *